United States Patent [19]

Molloy et al.

[11] 4,259,354
[45] Mar. 31, 1981

[54] METHOD OF TREATING ARRHYTHMIA

[75] Inventors: Bryan B. Molloy; Mitchell I. Steinberg, both of Indianapolis, Ind.

[73] Assignee: Eli Lilly and Company, Indianapolis, Ind.

[21] Appl. No.: 51,579

[22] Filed: Jun. 25, 1979

Related U.S. Application Data

[63] Continuation of Ser. No. 896,067, Apr. 13, 1978, abandoned.

[51] Int. Cl.$^3$ ............................................. A61K 31/14
[52] U.S. Cl. ..................................................... 424/329
[58] Field of Search ......................................... 424/329

[56] References Cited

U.S. PATENT DOCUMENTS

| 3,869,550 | 3/1975 | Dalgerd et al. ................. 424/329 X |
| 4,049,827 | 9/1977 | Molloy ................................. 424/330 |

OTHER PUBLICATIONS

Ariens (Ed), Molecular Pharm., Acd. Press, N.Y., vol. 1 1964, pp. 133, 164, 288–289, 310–313.
Taylor, Chem. Abs., vol. 60, 1963, p. 1003h.

*Primary Examiner*—Anna P. Fagelson
*Attorney, Agent, or Firm*—Charles W. Ashbrook; Arthur R. Whale

[57] ABSTRACT

A method of treating re-entrant arrhythmias comprising administering an effective dose of tetra-alkyl quaternary ammonium salt is provided. Pharmaceutical formulations containing a tetra-alkyl quaternary ammonium salt as the active ingredient are disclosed.

9 Claims, No Drawings

METHOD OF TREATING ARRHYTHMIA

This is a continuation of application Ser. No. 896,067, filed Apr. 13, 1978, now abandoned.

BACKGROUND OF THE INVENTION

A wide variety of drugs have been used in the treatment of disturbances in cardiac rhythm. The most commonly used antiarrhythmia drugs include digitalis, quinidine, procainamide, lidocaine and propranolol. Like most other drugs, toxic side effects generally accompany the use of certain of these drugs. A number of quaternary ammonium salts have been found to be effective antiarrhythmic agents with reduced side effects. Bretylium, for example, is an (o-bromobenzyl)ethyldimethylammonium salt which has been shown to be effective in the treatment of disturbances of ventricular rhythm that are not successfully abolished by conventional drugs.

While neither the causes of cardiac arrhythmias nor the modes of action of antiarrhythmic drugs are fully understood, several theories abound. It is generally accepted that differences in ionic concentrations and permeability of ionic channels across the cardiac membrane result in electrical potential differences that are somehow connected with arrhythmias. A great deal of research has accordingly been done in studying the responses of action potentials in many nerve and muscle fibers to various drugs. It is of interest to note that one of the actions of tetraethylammonium ion (a simple quaternary ammonium ion) is to specifically prolong the action potentials of many nerve and muscle fibers, see Loeb and Ewald, *J. Biol. Chem.*, 25, 377 (1916); Schmidt, *Arch. Ges. Physiol.*, 282, 357 (1965); and Ito et al., *The American Journal of Cardiology*, 41, 365 (1978).

An object of this invention is to provide a method for treating cardiac arrhythmia utilizing a certain class of tetra-alkyl quaternary ammonium salts. The compounds utilized in the method of this invention have demonstrated unexpected potency and efficacy in the prolongation of the action potential of cardiac Purkinje fibers. Pharmaceutical formulations containing such compounds are provided.

SUMMARY OF THE INVENTION

This invention relates to a method of treating cardiac arrhythmias comprising administering an effective dose of a tetra-alkyl quaternary ammonium salt of the formula

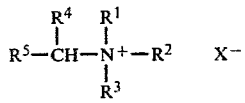

wherein:
$R^1$ and $R^2$ independently are $C_1-C_2$ alkyl;
$R^3$ is n-$C_1-C_8$ alkyl;
$R^4$ is hydrogen or methyl;
$R^5$ is n-$C_5-C_9$ alkyl; and
X is a therapeutically acceptable anion.

A preferred method of treatment comprises administering an antiarrhythmically effective dose of a compound of the above formula wherein:
$R^1$ and $R^2$ both are methyl or ethyl;
and $R^4$ is hydrogen.

An especially preferred method of treatment according to this invention comprises administering to a subject suffering from arrhythmia and in need of treatment or to a subject suspected of developing arrhythmia an effective dose of a compound selected from N,N,N-trimethylhexylammonium bromide,
N,N,N-trimethylheptylammonium bromide,
N,N,N-trimethyloctylammonium bromide,
N,N,N-trimethylnonylammonium bromide,
N,N,N-trimethyldecylammonium bromide,
N,N,N-trimethyl-1-methyloctylammonium bromide,
N,N,N-triethyloctylammonium bromide,
N,N-dimethyl-N-heptyloctylammonium bromide and
N,N-diethyl-N,N-dioctylammonium bromide.

This invention additionally provides a pharmaceutical formulation useful for treating cardiac arrhythmia comprising a compound of the above formula in combination with a pharmaceutically acceptable diluent, excipient or carrier therefor.

DETAILED DESCRIPTION OF THE INVENTION

The compounds which are to be used according to the method of this invention are either commercially available or can be prepared by routine procedures. For example, most of the compounds of the invention are prepared by simply reacting a tertiary amine with an alkylating agent such as an alkyl halide. The quaternary ammonium salt which is formed is normally highly crystalline and can be isolated by filtration and further purified if needed by recrystallization from common solvents such as methanol, ethanol and acetone.

The above formula defining the compounds to be used in the method of this invention defines a pharmaceutically acceptable anion by the symbol "X". Any of a number of therapeutically acceptable anions are comprehended, including anions such as chloride, bromide, p-toluenesulfonate, methanesulfonate, p-bromophenylsulfonate, phosphate, carbonate, oxalate, succinate, benzoate, acetate, and the like. A preferred and commonly used anion is bromide.

$R^3$ in the above formula is defined as a straight chain $C_1-C_8$ alkyl group, examples of which include methyl, ethyl, n-propyl, n-hexyl, n-heptyl and n-octyl. Similarly, $R^5$ is a straight chain $C_5-C_9$ alkyl group such as n-pentyl, n-hexyl, n-octyl and n-nonyl.

The method of treating arrhythmias according to this invention contemplates the use of a group of specific and potent antiarrhythmic drugs which are particularly useful in the treatment and prevention of ventricular fibrillation and other re-entrant arrhythmias by selectively prolonging the action potential, and consequently the refractoriness, of cardiac tissue. The compounds used in the method of this invention are unique in that they cause no inhibition of the rate of rise of the action potential at concentrations that prolong refractoriness. The method of treatment of this invention is particularly directed to the treatment and prophylactic prevention of arrhythmias such as ventricular flutter, ventricular fibrillation, ventricular pre-excitation, atrial fibrillation and supraventricular tachycardia.

According to the method of this invention, an antiarrhythmically effective dose of a tetra-alkyl ammonium salt of the above formula is administered to a subject suffering from an arrhythmia and in need of treatment or to a subject suspected of developing sudden death due to a re-entrant arrhythmia. It is contemplated that the method of this invention will find extensive prophylactic use in the prevention of sudden death due to arrhythmia. The dose of drug to be administered according to this invention normally will be from about 200 μg/kg. to about 800 μg/kg. The particular dosage in any treatment will of course depend upon factors such as the compound administered, the rate of administration and the particular subject being treated.

The antiarrhythmic drugs contemplated by the method of this invention can be administered either orally or parenterally. For the prophylactic treatment of reentrant arrhythmias, it is preferred to formulate the compounds for convenient oral administration. For example, a tetra-alkyl ammonium salt such as N-methyl-N-ethyl-N-butyloctylammonium p-toluenesulfonate can be admixed with suitable excipients such as sucrose and starch powder and compressed into tablets or encapsulated into pulvules. Such formulations are administered orally to a subject suspected of developing sudden death due to a re-entrant arrhythmia. The formulations will be composed of sufficient active tetra-alkyl quaternary ammonium salt so that the daily dosage for a subject weighing about 70 kg. will be about 20 to about 35 mg.

For the treatment of subjects who have suffered an arrhythmia and are in need of treatment to effect conversion of the arrhythmia to a normal sinus rhythm, intravenous administration of a tetra-alkyl quaternary ammonium salt having the above formula is preferred according to the method of this invention. For example, a human subject who has experienced or is experiencing an arrhythmia such as a ventricular fibrillation or flutter can be administered intravenous doses of a drug such as N,N,N-triethyloctylammonium phosphate dissolved in diluents such as 10% dextrose in water or isotonic saline. The dosage regimen will be from about 5 to about 15 mg. of active drug infused every six to ten hours for a subject weighing about 60 kg. Once the arrhythmia has been successfully converted to a normal sinus rhythm, the normal condition can be maintained by a route of administration more suited to the treatment of an outpatient. For instance, the subject can be maintained by intramuscular injections of a tetra-alkyl quaternary ammonium salt of the above formula at doses of about 5 mg. given about two times each day or more often as the severity of the condition requires. Preferably all maintenance therapy, as well as prophylactic treatment, will be accomplished by oral administration as hereinbefore pointed out.

While the above described modes of administration are preferred by the method of this invention, alternative routes are additionally contemplated by the invention. In particular, the tetra-alkyl quaternary ammonium salts can be formulated for administration as suppositories. Alternatively the active drugs can be admixed in the form of a slow release buccal seal.

A further embodiment of this invention are pharmaceutical formulations useful in the treatment of arrhythmia according to the above described method. For the preferred oral therapeutic administration, the active compounds can be incorporated with excipients and used in the form of tablets, troches, capsules, syrups, suspensions, elixirs, wafers, buccal seals, and the like. Such compositions and preparations will contain at least 0.1% of the active drug. The amount of active ingredient in any such therapeutically useful compositions is adjusted so that a suitable dosage as described hereinabove will be obtained. Clearly, preferred formulations according to the present invention are prepared so that an oral dosage unit form contains from about 5 to about 15 mg. of active compound. Such compositions are administered from 1 to about 3 times per day to a subject weighing from about 50 to about 90 kg.

For intramuscular injection, the quaternary ammonium salts are dissolved in solutions such as isotonic glucose or the like. The concentrations of active drug generally will be about 1 to about 30 mg./ml.

In addition to the active drug, the parenteral solutions contemplated by this invention may contain preservatives and further diluents such as phenethyl alcohol, methyl and propyl parabens and thimerosal. Compounds often employed as antioxidants include sodium metabisulfite, sodium bisulfite and the like.

The tetra-alkyl quaternary ammonium salts which are the active compounds employed in the method of this invention have been demonstrated to be unusually potent antiarrhythmic drugs in tests designed to show such utility. Standard electrophysiological techniques have been utilized to measure the effects of the drugs on resting potential, action potential amplitude, duration, rate of rise and effective refractory periods of normal canine Purkinje fibers. The fibers were superfused in vitro with Ringer's solution at 35° C. and stimulated at 1 Hz during the assays. The following Table demonstrates the percentage prolongation of action potential duration attributable to a tetra-alkyl quaternary ammonium salt in the Purkinje fibers.

TABLE

| Compound Tested | Molar Concentration | Percent of Prolongation |
|---|---|---|
| N,N,N-triethyloctyl-ammonium bromide | $3 \times 10^{-7}$ | 27.3 |
| N,N,N-trimethyloctyl-ammonium bromide | $3 \times 10^{-7}$ | 13.6 |
| N,N,N-trimethylheptyl-ammonium bromide | $1 \times 10^{-5}$ | 33.0 |
| N,N,N-trimethylhexyl-ammonium bromide | $1 \times 10^{-5}$ | 28.1 |
| N,N,N-trimethyl-1-methyl-octylammonium bromide | $3 \times 10^{-7}$ | 23.2 |
| tetraethylammonium bromide | $1 \times 10^{-5}$ | 0 |

The compounds used in the method of this invention additionally have demonstrated in vitro utility in prolonging action potential and refractoriness of cardiac tissue. Certain compounds have been tested in dogs subjected to electrically-induced ventricular fibrillation, and have effected a marked decrease in the vulnerability of cardiac tissue to fibrillation. The compounds also have been demonstrated to convert flutter, ventricular fibrillation and rapid tachycardia to normal sinus rhythm by prolonging the refractoriness. Because of the specific prolongation of refractoriness thus shown by the compounds comprehended by the method of this invention, the tetra-alkyl quaternary ammonium salts of the above formula are useful in situations where rapid inappropriate ventricular rates are present, specifically in cases of ventricular pre-excitation tachyarrhythmia.

The following detailed examples serve to illustrate general methods of preparation of tetra-alkyl quaternary ammonium salts as well as typical formulations of such compounds.

EXAMPLE 1

N,N,N-Triethyloctylammonium bromide

A solution of 10 g. of N,N-diethyloctylamine in 82 ml. of ethyl bromide was heated to reflux and stirred for twenty hours. The reaction mixture was cooled to room temperature and the excess ethyl bromide was removed by evaporation under reduced pressure to leave a solid residue. The solid thus formed was crystallized from 150 ml. of 90% ethyl acetate in acetone to provide 11.334 g. of N,N,N-triethyloctylammonium bromide. M.P. 115°–117° C.

Analysis calc. for $C_{14}H_{32}BrN$: Theory: C, 57.13; H, 10.96; N, 4.76; Br, 27.15. Found: C, 56.83; H, 10.69; N, 4.68; Br, 27.06.

EXAMPLE 2

N,N-Dimethyl-N,N-dioctylammonium bromide

A solution of 48.3 g. of dioctylamine in 51 ml. of 90% aqueous formic acid containing 49 ml. of 37% aqueous formaldehyde solution was heated to 100° C. for thirty minutes and then stirred at room temperature for fifteen minutes. The reaction mixture was again heated to 100° C. and then stirred at that temperature for twelve hours. The reaction mixture next was cooled, acidified by the addition of 180 ml. of 4 N hydrochloric acid, and then concentrated to dryness by evaporation of the solvent. The residual oil was dissolved in 200 ml. of water and made alkaline by the addition of 5 N sodium hydroxide. The aqueous alkaline solution was extracted with diethyl ether. The ethereal solution was then extracted twice with 2 N sulfuric acid. The acidic extracts were combined, basified by the addition of 5 N sodium hydroxide, and the product was extracted therefrom into diethyl ether. The ethereal extracts were combined, washed with water, dried, and the solvent was removed by evaporation to provide 50.45 g. of N-methyl-N,N-dioctylamine.

Following the general procedure of Example 1, 5.0 g. of N-methyl-N,N-dioctylamine was reacted with methyl bromide in diethyl ether to provide, after crystallization from diethyl ether, 6.89 g. of N,N-dimethyl-N,N-dioctylammonium bromide.

Analysis calc. for $C_{18}H_{40}BrN$: Theory: C, 61.70; H, 11.51; N, 4.00; Br, 22.80. Found: C, 60.19; H, 11.18; N, 3.71; Br, 23.20.

EXAMPLE 3

N,N,N-Trimethyl-1-methyloctylammonium bromide

One hundred grams of 2-hydroxynonane was reacted with 188.2 g. of phosphorous tribromide in 300 ml. of benzene containing 0.2 ml. of pyridine to provide, after distillation, 81.5 g. of 2-bromononane. B.P. 85°–88° C./15 torr.

A solution of 30 g. of 2-bromononane in 300 ml. of ethanol was reacted with 120 ml. of dimethylamine at 100° C. for twenty-four hours to provide, after purification by acid and base extractions, 20.7 g. of N,N-dimethyl-1-methyloctylamine. The amine so formed was further purified by conversion to the oxalate salt and crystallization of the salt from ethyl acetate. M.P. 97°–98° C.

Five grams of N,N-dimethyl-1-methyloctylaminium oxalate was reacted with 5 N sodium hydroxide to give 3.3 g. of the free amine. The amine was dissolved in 150 ml. of diethyl ether and the ethereal solution was saturated with methyl bromide gas for fifteen minutes, and then stirred at room temperature for twelve hours. The solvent was next removed by evaporation and the residue was crystallized from acetone to provide 1.3 g. of N,N,N-trimethyl-1-methyloctylammonium bromide. M.P. 230° C. (dec.).

Analysis calc. for $C_{12}H_{28}NBr$: Theory: C, 54.13; H, 10.60; N, 5.26; Br, 30.01. Found: C, 54.21; H, 10.01; N, 5.31; Br, 29.40.

EXAMPLE 4

N,N,N-Trimethylheptylammonium bromide

A solution of 90 g. of heptyl bromide in 250 ml. of acetone containing 30 g. of trimethylamine was heated to reflux and stirred for twelve hours. The reaction mixture was cooled to 5° C. in an ice-water bath, and the crystallized produced was collected by filtration. The product was recrystallized from ethanol and diethyl ether to provide 81.4 g. of N,N,N-trimethylheptylammonium bromide. M.P. 188°–190° C.

Analysis calc. for $C_{10}H_{24}NBr$: Theory: C, 50.42; H, 10.16; Br, 33.55. Found: C, 50.30; H, 10.22; Br, 33.67.

EXAMPLES 5–8

Following the general procedure set forth in Example 1, the following quaternary ammonium salts were prepared:

N,N,N-Trimethylnonylammonium bromide. M.P. 224° C. (dec.).

Analysis calc. for $C_{12}H_{28}NBr$: Theory: C, 54.13; H, 10.60; N, 5.26; Br, 30.01. Found: C, 54.36; H, 10.54; N, 5.49; Br, 30.00.

N,N,N-Trimethyloctylammonium bromide. M.P. 206°–208° C.

Analysis calc. for $C_{11}H_{26}NBr$: Theory: C, 52.38; H, 10.39; N, 5.55; Br, 31.68. Found: C, 52.25; H, 10.31; N, 5.35; Br, 31.48.

N,N,N-Trimethylhexylammonium bromide. M.P. 172°–174° C.

Analysis calc. for $C_9H_{22}BrN$: Theory: C, 48.22; H, 9.89; N, 6.25; Br, 35.64. Found: C, 48.20; H, 10.08; N, 6.33; Br, 35.72.

N,N,N-Trimethyldecylammonium bromide. M.P. 230° C. (dec.).

Analysis calc. for $C_{13}H_{30}BrN$: Theory: C, 55.71; H; 10.79; N, 5.00; Br, 28.51. Found: C, 55.50; H, 10.51; N, 5.25; Br, 28.35.

EXAMPLE 9

N,N-Diethyl-N-heptyloctylammonium bromide

Octylamine was acrylated with one equivalent of heptanoyl chloride to provide N-octylhexanecarboxamide. The amide was reduced by reaction with diborane in tetrahydrofuran to provide N-heptyloctylamine. To a cold stirred solution of 19.79 g. of N-heptyloctylamine and 23.4 g. of sodium carbonate in 82 ml. of acetone and 82 ml. of water was added dropwise over thirty minutes a solution of 13.7 ml. of acetyl chloride in 164 ml. of acetone. The reaction mixture was stirred for twelve hours following complete addition, after which time the solvent was removed by evaporation under reduced pressure. The residual oil was dissolved in diethyl ether and washed with water and with 2 N hydrochloric acid. The ethereal solution then was dried and the solvent was removed by evaporation to provide 22.48 g. of N-heptyl-N-octylacetamide.

The amide thus formed was reduced by reaction with diborane to provide, after purification by acid and base extraction, 19.68 g. of N-ethyl-N-heptyloctylamine.

The amine was further purified by conversion to the oxalate salt and crystallization of the salt from ethyl acetate. M.P. 85°–87° C. The amine oxalate salt was reacted with sodium hydroxide to provide the free amine, which next was reacted with ethyl bromide at reflux temperature for sixty hours to provide, after crystallization from ethyl acetate, 5.87 g. of N,N-diethyl-N-heptyloctylammonium bromide. M.P. 65°–70° C.

Analysis calc. for $C_{19}H_{42}BrN$: Theory: C, 62.62; H, 11.62; N, 3.84; Br, 21.92. Found: C, 62.39; H, 11.40; N, 3.83; Br, 21.89.

EXAMPLE 10

Preparation of 25 mg. Tablets

N,N,N-trimethylammonium bromide: 25 mg.
Lactose: 105 mg.
Corn starch: 168 mg.
magnesium stearate (1%): 2 mg.

The above ingredients are blended with the magnesium stearate as a lubricant. The mixture is compressed into tablet form. Such tablets are administered to a human for the treatment of re-entrant arrhythmia at the rate of 1 to about 3 tablets per day or as needed.

EXAMPLE 11

Preparation for Oral Suspension

N,N-Diethyl-N,N-dioctylammonium bromide: 500 mg.
Sorbitol solution (70% N.F.): 40 ml.
Saccharin: 10 mg.
Cherry flavor: 50 mg.
Distilled water: 100 ml.

The above ingredients are made into a syrup which contains approximately 5 mg. of active ingredient per ml.

We claim:

1. A method of treating re-entrant arrhythmias in humans suffering from such arrhythmias and in need of treatment or in humans suspected of developing a re-entrant arrhythmia comprising administering to such subject an antiarrhythmically effective dose of a compound of the formula

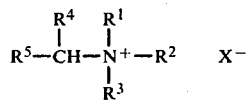

wherein:
 $R^1$ and $R^2$ independently are $C_1$–$C_2$ alkyl;
 $R^3$ is n-$C_1$–$C_8$ alkyl;
 $R^4$ is hydrogen or methyl;
 $R^5$ is n-$C_5$–$C_9$ alkyl; and
 X is a therapeutically acceptable anion.

2. A method according to claim 1 wherein in the compound administered, $R^1$ and $R^2$ both are methyl or ethyl.

3. A method according to claim 2 wherein in the compound administered, $R^3$ is methyl or ethyl.

4. The method of claim 3 wherein the compound administered is N,N,N-trimethyl-1-methyloctylammonium bromide.

5. A method according to claim 3 wherein in the compound administered, $R^4$ is hydrogen.

6. A method according to claim 5 wherein the compound administered is selected from the group consisting of:
 N,N,N-trimethylheptylammonium bromide;
 N,N,N-trimethylhexylammonium bromide;
 N,N,N-trimethylnonylammonium bromide;
 N,N,N-trimethyloctylammonium bromide;
 N,N,N-trimethyldecylammonium bromide; and
 N,N,N-triethyloctylammonium bromide.

7. A method according to claim 2 wherein in the compound administered, $R^3$ is heptyl or octyl.

8. A method according to claim 7 wherein in the compound administered, $R^4$ is hydrogen.

9. A method according to claim 8 wherein the compound administered is selected from the group consisting of:
 N,N-diethyl-N-heptyloctylammonium bromide and
 N,N-dimethyl-N,N-dioctylammonium bromide.

* * * * *